United States Patent [19]

Glassman

[11] Patent Number: 4,503,031

[45] Date of Patent: Mar. 5, 1985

[54] SUPER-FAST-STARTING-SUSTAINED RELEASE TABLET

[76] Inventor: Jacob A. Glassman, 1680 Michigan Ave., Miami Beach, Fla. 33139

[21] Appl. No.: 588,904

[22] Filed: Mar. 12, 1984

Related U.S. Application Data

[63] Continuation-in-part of Ser. No. 436,930, Dec. 17, 1982, abandoned.

[51] Int. Cl.³ .............. A61K 9/24; A61K 9/46; A61K 9/44
[52] U.S. Cl. .................. 424/15; 424/21; 424/44
[58] Field of Search ............. 424/15, 21, 44; 264/113

[56] References Cited

U.S. PATENT DOCUMENTS

| | | | |
|---|---|---|---|
| 536,155 | 3/1895 | Noyes | 424/44 |
| 2,105,690 | 1/1938 | Greenblatt | 424/44 |
| 2,297,599 | 9/1942 | Wilen | 424/44 |
| 2,312,381 | 3/1943 | Bickenheuser | 424/44 |
| 2,809,917 | 10/1957 | Hermelin | 424/21 |
| 2,951,792 | 9/1960 | Swintosky | 424/21 |
| 2,953,497 | 9/1960 | Press | 424/20 |
| 2,996,431 | 8/1961 | Barry | 424/20 |
| 3,044,938 | 7/1962 | Halley | 424/19 |
| 3,048,526 | 8/1962 | Boswell | 424/21 |
| 3,096,248 | 7/1963 | Rudzki | 424/31 |
| 3,109,775 | 11/1963 | Shepard et al. | 424/20 |
| 3,115,441 | 12/1963 | Hermelin | 424/34 |
| 3,146,169 | 8/1964 | Stephenson et al. | 424/19 |
| 3,336,200 | 8/1967 | Krause et al. | 424/19 |
| 3,344,029 | 9/1967 | Berger | 424/19 |
| 3,388,041 | 6/1968 | Gans et al. | 424/20 |
| 4,025,613 | 5/1977 | Guy et al. | 424/21 |
| 4,083,951 | 4/1978 | Goudie et al. | 424/44 |
| 4,122,157 | 10/1978 | Huber | 424/21 |
| 4,140,755 | 2/1979 | Sheth et al. | 424/19 |
| 4,353,887 | 10/1982 | Hess et al. | 424/15 |
| 4,361,545 | 11/1982 | Powell et al. | 424/19 |

FOREIGN PATENT DOCUMENTS

| | | | |
|---|---|---|---|
| 2834226 | 2/1980 | Fed. Rep. of Germany | 424/15 |
| 442266 | 8/1912 | France | 424/15 |
| 53-127821 | 8/1978 | Japan | 424/15 |
| 15161 | of 1903 | United Kingdom | 424/44 |
| 1233055 | 5/1971 | United Kingdom | 424/19 |
| 1372040 | 10/1974 | United Kingdom | 424/15 |
| 2078518A | 1/1982 | United Kingdom | 424/15 |

Primary Examiner—Shep K. Rose
Attorney, Agent, or Firm—Elmer L. Zwickel

[57] ABSTRACT

A super-fast-starting, slow release medicinal tablet, wherein the tablet is comprised of two layers of compressed matrix that are fused together by means of a readily dissolvable adhesive substance, and in which one of the layers is a lightly compressed top layer containing a pure unadulterated, uncoated, active drug and which has one or more radial grooves in it's top surface to enhance rapid breakdown of the tablet; and the other layer has a strongly compressed portion comprised of a medically inert or inactive matrix having embedded throughout a multitude of pellets, each containing an active ingredient and having enteric coatings of various thicknesses so as to variably delay disintegration of the pellets.

9 Claims, 6 Drawing Figures

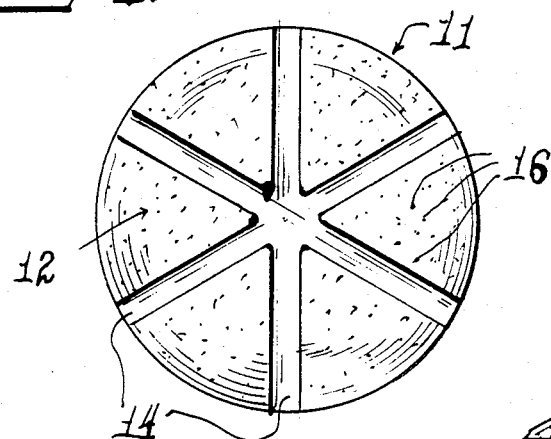
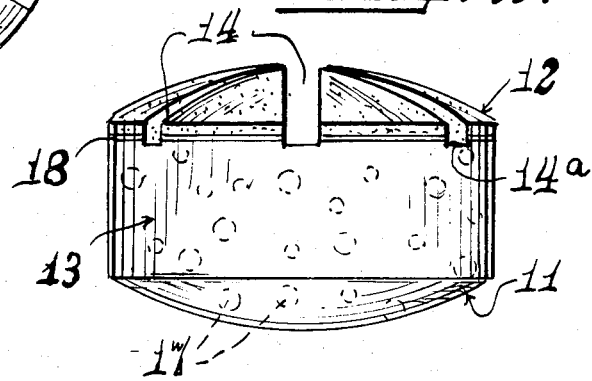
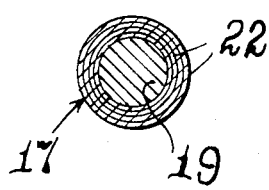
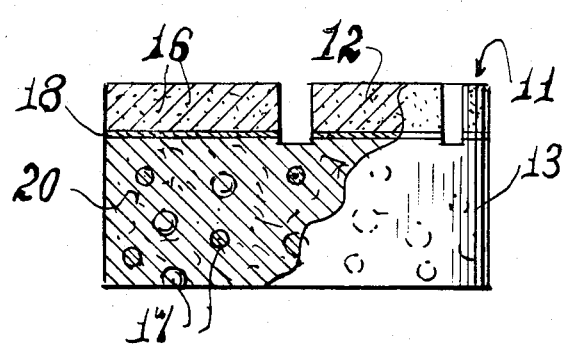
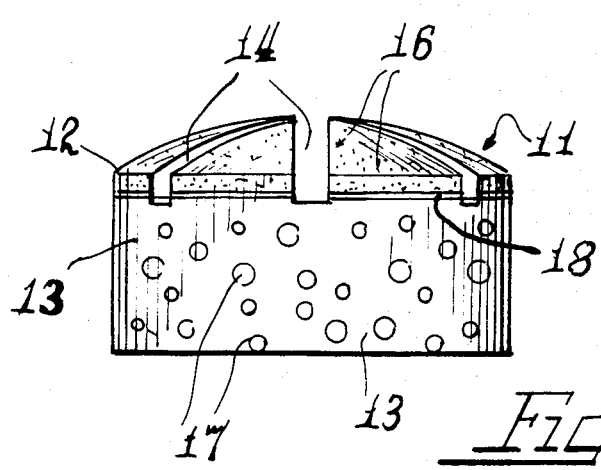

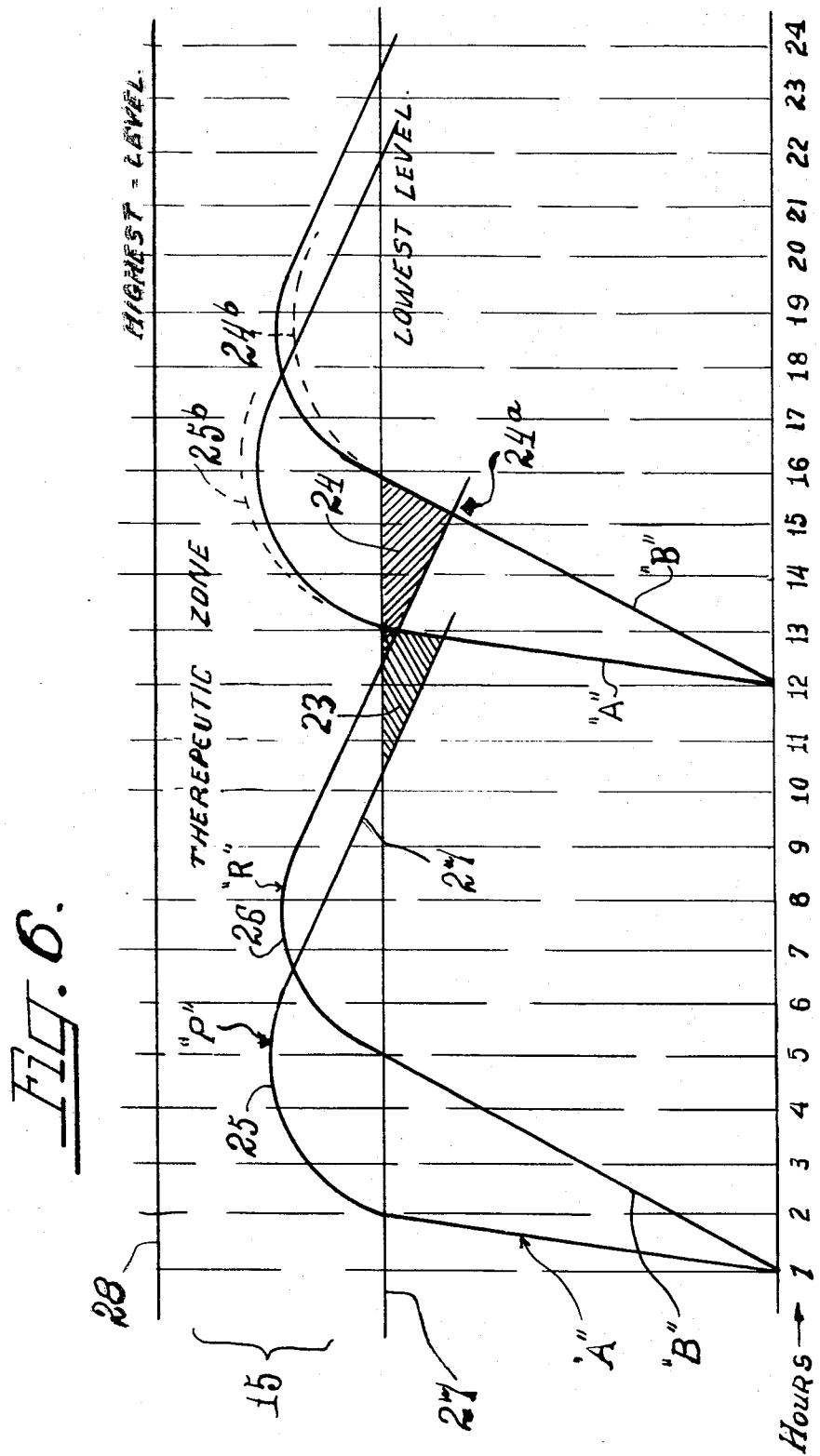

SUPER-FAST-STARTING-SUSTAINED RELEASE TABLET

This application is a continuation-in-part of my co-pending Application Ser. No. 436,930, Filed Dec. 17, 1982, abandoned.

The present invention relates to improvements in pharmaceutical tablets and to the process of manufacturing same.

Multi-coated sustained release or delayed action pharmaceutical tablets are known and are disclosed in U.S. Pat. Nos. 3,080,294; 2,853,420 and 2,996,431. These patents are concerned primarily with a slow starting and slow sustained release of it's medicaments. The present disclosure pertains to the provision of a medicated tablet comprising two layers, the tightly compressed bottom layer of which contains medicament pellets coated with v a few or many enteric coatings resistant to stomach juices, so as to delay release of the medicament until after the coating has been dissolved or substantially dissolved by action of intestinal fluids. However, the top layer, composed of a lightly compressed corn starch or talc base, may by way of example and not limitation, contain pure, unadulterated, uncoated active medicament, such as, to mention a few, theophylline drugs as well as analgesics, anti-histamines, nitroglycerine, theophylline derivatives, aspirin, and acetaminophens, all of which may be speedily released within the stomach for immediate relief of such symptoms as pain, asthma, allergy, etc. Specifically, the hereindisclosed medicated tablet is primarily suitable whenever a very rapid drug absorption and therapeutice effect is desirable. Such clinical emergencies exist in asthmatics, in anginal cardiac situtions and in various acute allergic conditions.

Further, the within described tablet works rapidly in stages, or in sequence—that is, the drug is first released fast and then absorbed fast to enter the therapeutic zone in the blood for that specific drug and for immediate thereputic response. The drug is then released over 4, 6 or 12 hour periods to maintain the drug level within the therapeutic zone while simultaneously maintaining the desired therapeutic effect. This tablet being the fastest of all tablet disintegration rates, serves to keep the diminishing therapeutic curve from dropping below the lowest level of the therapeutic zone—by having it's fastest rising absorption curve enter the therapeutic zone to keep the therapeutic curve from dropping out of the therapeutic zone. Thus the herein described tablet keeps the active drug ingredient constantly within the therapeutic zone with a minimum of valleys and peaks and better maintains unbroken clinical therapeutic response.

The foregoing and other objects of the invention will be more fully understood upon reference to the accompanying description and drawings, in which:

FIG. 1 is an enlarged top plan view of the tablet;

FIG. 2 is an enlarged side elevational view of the tablet illustrated in FIG. 1, and which is bi-convex shaped;

FIG. 3 is an enlarged side elevational view of a flat bottom and convex top type of tablet;

FIG. 4 is an enlarged view, partially in section, of a flat top and flat bottom type of tablet which also embodies features of the invention;

FIG. 5 is an enlarged central sectional view through an embedded pellet provided with a medicinal interior and several protective coatings; and FIG. 6 is a graph illustrating predictable differences between a long-acting tablet and the super-fast-starting sustained-release tablet herein disclosed.

Referring now to the disclosure in the accompanying drawings, the super-fast-starting sustained release timed tablet 11 is comprised of two layers; a minor layer 12 and a major bottom layer 13. These layers are fused together by compression. In forming the layers, the major bottom layer 13 is strongly pressed while the upper or top layer 12 is lightly compressed. Preferably, the top layer is multiply scored with deep depressions 14, preferably diametrically arranged, to facilitate super-fast separation and lift-off of the top layer 12 with fragmentation and dissolution of the medicaments embedded therein.

As illustrated in FIG. 6, hereinafter discussed in detail, failure of a long-acting theophylline tablet to act quickly permits an undesirable latent period to exist which lag is graphically recognized when a follow-up dose fails to reinforce or quickly pick up the preceding declining drug-curve and elevate it back up into the range of the therapeutic zone 15. For theophylline (anhydrous), the therapeutic zone ranges from 10 mcg/ml. to 20 mcg/ml.

As noted, the disclosed top layer of the tablet breaks down rapidly. It's breakdown toward final disingration and absorption takes place in the most rapid and predictable steps or stages, all to be fully explained hereinafter.

The top layer 12 of the tablet contains the pure unadulterated and uncoated active drug 16. It may be in powdered, crystal or micro-crystalline form (preferably in it's purest form) so that quick release, quick absorption and quick therapeutic effects are obtained. All this occurs before coated pellets 17 contained in the bottom portion 13, and later referred to in detail, are slowly breaking up physically. In other words, the top layer 12, containing the uncoated drug 16 in it's purest form, releases same fast enough to prevent an acute attack, for example, an asthmatic attack, an acute allergic reaction, a severe anginal pain. The top layer 12 disassociates or breaks up fast; the drug absorbs faster, and in athma, a therapeutic blood level of between 10 and 20 mcg/ml. is reached in the fastest possible manner.

In order to accomplish this end, the top layer 12 contains a pure drug 16 in it's finest form. To assist quicker dissolution and separation of the top layer 12, a small quantity of a mixture of sodium bicarbonate (or potassium bicarbonate) may be added to the top layer mix. The rapid reaction between these two agents liberates carbon dioxide ($CO^2$) that further assists the disintegration of the drug 16, thus resulting in a much faster therapeutic start. The mid, or central, thin layer 18 of talc, or talc and starch, serves to keep the top layer cemented to the bottom layer 13 detachably so as to allow for quick "explosive" separation and lift-off of the upper layer from the lower layer. A mixture of a bicarbonate and an acid is incorporated in layer 18.

The bottom layer 13 of the tablet achieves the continuous but slow and controlled release of an active medicament 19 in the coated pellets 17. This bottom layer 13 is made up of a medically inert or inactive matrix 20 such as sugar, corn starch, or any suitable material that has embedded therein throughout, a multitudious number of the variable coated pellets 17, each containing the medicament 19. The number of coatings or layers 22 covering the drug-pellets 17 may vary from as few as 25 to as many as 250. Consequently, the pellet with the greatest number of coatings 22 has the slowest disassociation rate and release of active medicament 19. The variable multiple coatings on the pellets, when exposed to the gastro-intestinal secretions release their drug ingredient slowly, but unpredictably.

The six, eight or twelve hour release of the pellets may be very slow, too slow, or not at all. The only positive and predictable feature of the pellet-containing bottom layer 13 is that it's matrix 20 slowly releases the active medicament 17 which is then slowly absorbed, hence making it impossible to obtain any super-fast starting therapeutic action. No long acting tablet on the market today can achieve such result. In other words, blood levels are to slow to develop, and therefore therapeutic levels are also too slow to develop. This means that the overall desired therapeutic action or result is delayed or too slow in arriving. The slow action time of the sustained release drugs, invariably fail to act quickly and decisively. The reason for this being that most time-release tablets take from one to four hours to enter the therapeutic zone of the blood serum 15 (see FIG. 6). The uncoated pure drug particles 16, in the moderately conpressed layer 12, are rapidly released into solution, and absorbed faster and reach the therapeutic blood level faster (See FIG. 6 #30) and most important obtain the fastest and most immediate initial therapeutic response. The time required may vary from one-half hour to one hour. All will be better explained hereinafter with respect to the FIG. 6 disclosure.

The cohesion of the top layer 12 to the bottom layer 13 is accomplished with a lighter form of compression, and the top layer is then deeply and/or multiply scored, as at 14. These scores are deep enough to penetrate through the top layer and extend a very short distance 14a into the pellet containing bottom layer 13. Finally, before the top layer is poured or otherwise arranged over the bottom layer, a very fine layer of talc and/or starch 18 may be spread over the top surface of the bottom layer. The fine layer of talc or corn starch assists the top layer 12 to separate, lift off and disassociate into it's finest form and be absorbed more rapidly from the stomach and intestines. The talc, may if desired, be combined with any other suitable binding agent to assist in binding the layers together as well as releasing them during the disassociation sequence of the tablet. The effervescent combination is admixed with the mid-layer 18 as well as with the top layer 12. Layer 18 mainly, is comprised of a suitable effervescent salt combination such as talc, starch and/or sugar/

The final tablet structure 11 becomes a useful double-tablet, that functions synergistically to effect a new result, namely: an ultra fast starting, slow-time release tablet. This tablet finds new and useful application in various medical areas that demand the fastest possible initial action attainable and slow-release follow-up, for the continued maintenance of the therapeutic drug action over long predictable periods of time.

To be more specific, the fast-starting long-acting tablet 11 breaks down very rapidly, yet in predictable steps or stages. The physical and chemical changes start to take place the instant wetnes (water or gastric juices) activates the middle solid layer 18 of acid-base effervescent salts. The rapid events occur in sequence as follows:

First: The top medicated layer 12 lifts off the effervescent base layer and the bottom layer 13 falls away by itself;

Second: The top layer 12 fragments into predictable equal segments depending upon the topside groove design 14;

Third: Each top layer segment which includes it's own effervescent salt mixture, undergoes rapid dissolution and complete disintegration as it enters into solution; and Fourth: The bottom slow release layer 13 falls away from layer 18 and starts to break down slowly—the rate depending upon what type of acceptable slow-release mechanism is selected.

The selected effervescent salt combination that is thoroughly admixed with the active drug ingredient of the top-layer is synergistically combined with lubricants such as talc, and sugar so as obtain greater compressive cohesiveness between top deeply grooved layer and the solid effervescent mit-layer below. The adherance of the deeply grooved top layer to the base effervescent layer must be firm because the deep grooves completely segmentalize the top layer—except for its attached base. When interaction between the effervescent mid layer and moisture takes place, the top layer fragments into segments and have only to lift-off from their bases and start to disintegrate. Such disintergration will further be speeded up by the fact that the segments are exposed on all six sides to the moisture or juices.

Turning now to FIG. 6, the curve 32 illustrates a projected serum level of Theophylline (uncoated tablet) given in a dosage of 5 mg/kgm body weight. Curve 31 illustrates a projected serum level of Theophylline, given a dosage of 10 mgm/kgm body weight. Curve 30 illustrates a projected estimation of serum level of Theophylline (in the present disclosure) in a dosage of 15 mgm/kgm body weight; one-third (approximately) of the dose in the upper fast-acting portion 12, and two-thirds of the dose in the lower sustained release (S/R) portion 13; approximately at a ratio of 2:1.

The curve 33 shows how another dosage of the herein tablet taken orally at a 12 hour interval, will prevent peaks and troughs, and would push the curve (30) upwardly off the lowest blood level (27) into the Therapeutic Zone. The predicted mean therapeutic level is represented by line 35, for the entire prescribed long sustained time interval.

The FIG. 6 graph clearly illustrates that neither a plain coated tablet of Theophylline, nor the slow-acting double dose sustained-release (S/R) tablet is capable alone of rapidly and predictably entering the Therapeutic Zone. The herein disclosed super-fast-acting, slow-release tablet (S/R) predictably enters into the Therapeutic Zone in the shortest possible time (less than one hour). That is 4–5 times faster than any known sustained release tablet, and it offers immediate and lasting therapeutic relief covering a period of 12 or more hours.

Studies in asthmatic children have shown that single dosage or uncoated tablets of Theophylline, or like acting drugs, do not absorb fast enough nor do they enter into the Therapeutic Zone (curve 32). These same studies also have shown that single dosage theophylline long acting pellet type tablets (curve 31) also does not enter into the Therapeutic Zone. Such studies have definitely shown that the combined use of an uncoated tablet and a sustained release tablet, does in fact allow for the entrance of the Theophylline curve (30) well into the Therpeutic Zone 27. Applicant has constructed a table made up of (2) portions: an upper minor portion 12, and a lower major portion 13 which, after being swollowed, allows the upper unadulterated uncoated microcrystalline medicament to break up with super-speed and absorb in the fastest time possible, while the lower pellet-matrix combination containing the regular medicament in it's pellets releases the medicament slowly in the small intestinal tract and successfully covers a longer but sustained period of absorption.

Note how curve 30 enters and remains consistently longer within the Therapeutic Zone (12 hours or longer) depending upon the dosage selected. Also, the curve 30 clearly illustrates how an asthmatic or allergic attack, in it's acute and urgent form, can be effectively treated within the hour with the new super-fast-action, slow-release tablet, while curves 31 and 32 clearly indicate that this cannot be accomplished with either uncoated or pellet-matrix tablets given alone and apart, under 4 hours. From the FIG. 6 graph, one may conclude that the instant tablet 11 is far superior to the regular long action tablet primarily because it offers two distinct and important functions instead of but one, i.e.: super-fast-starting; super fast absorption, and time release of medicament. To accomplish the earliest acting and most consistent therapeutic blood level has been the ultimate goal of the sustained release tablet, but only the dual functional tablet as disclosed herein can effectively attain that goal.

The invention is not to be limited to the exact dosage and ratios mentioned, nor is it limited to the medicaments selected by way of example, or to the exact number of coatings on the pellets or granules nor to any particular matrix material, binders, separating materials or effervescent acid-base mixture or manufacturing processes. It is especially possible in accordance with the invention to obtain suspension in a predetermined manner to increase one or the other of the desired effects.

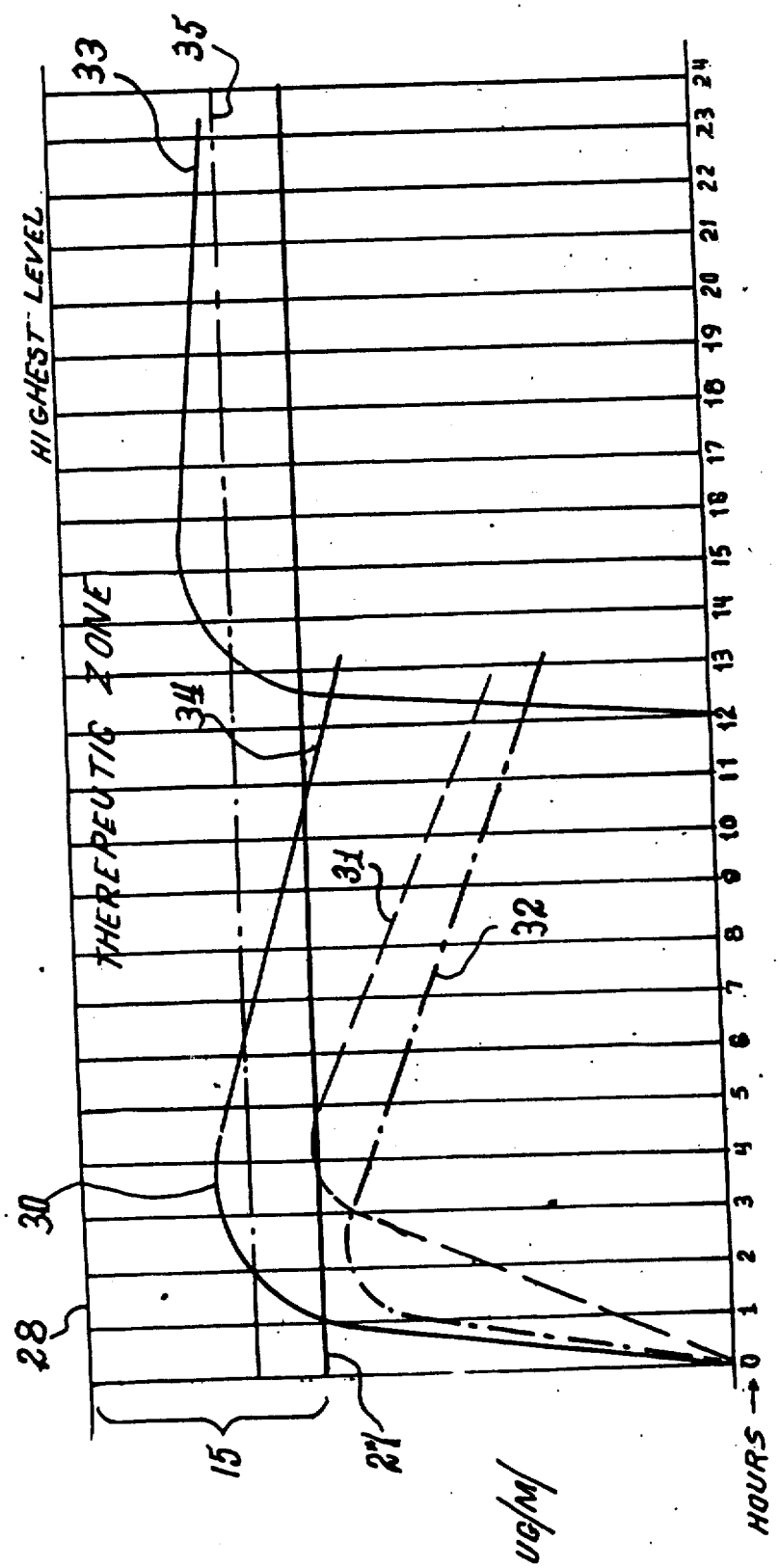

I claim:

1. 
(a) A medically active tablet including top and bottom layers of compressed medically inert granular-like matrix material,
(b) a number of pure unadulterated pellets of active medicament embedded in the matrix material of the bottom layer
(c) an enteric coating on each of said pellets resistant to stomach juices,
(d) the matrix material of the said bottom layer being strongly compressed to resist rapid release of the pellets,
(e) said top layer being lightly compressed, a quantity of pure unadulterated uncoated pellets of active medicament embedded in the matrix material of the top layer,
(f) at least one groove in the said top layer dividing it into segments, and
(g) a midlayer including an effervescent mixture of a bicarbonate and an acid arranged between said two layers,
(h) said midlayer securing said two layers together and being subject to rapid dissolution by fluid and stomach juices to separate the segments from the bottom layer and obtain quick dissolution and immediate absorption of the active drug in said segments and a super-fast therapeutic start.

2. The tablet recited in claim 1, wherein release lift-off of the top layer segments enhances rapid fragmentation and dissolution of the top layer.

3. The tablet recited in claim 1, wherein there are several deep grooves in the top layer dividing it into independent segments down to the bottom layer.

4. The tablet recited in claim 1, wherein the lightly compressed top layer includes a proportioned effervescent mixture of sodium bicarbonate and an acid.

5. The tablet recited in claim 1, wherein the lightly compressed mid-layer includes a desired and proportioned mixture of sodium bicarbonate and citric acid which upon being moistened liberates carbon dioxide.

6. The tablet recited in claim 1, wherein there are a multitude of deep-cut grooves in the top layer dividing said layer into a multitude of segments to hasten their separation from the bottom layer and increase the rate of drug absorption and therapeutic action.

7. A medically active tablet consisting of an upper and a lower layer of compressed medicinally inert granular like matrix material, the lower layer having a number of enteric-coated medicinal pellets embedded therein, said lower layer being strongly compressed to resist rapid release of the medicaments therein, the upper layer including a quantity of pure unadulterated crystalline and micro-crystalline active medicaments admixed with an effervescent mixture to assist quicker dissolution of the upper layer embedded in the matrix material of said upper layer, said top layer being lightly compressed to allow for early disassociation from the bottom layer and rapid dissolution of the medicaments contained therein, a mid-layer arranged between the said two layers, said mid-layer including medicinally inert granular-like matrix material and an effervescent mixture of a bicarbonate and an acid to assist separation and disintegration of the top layer and quicker absorption of the active drug, thus resulting in a much faster therepeutic start.

8. The tablet recited in claim 7, wherein the upper surface of the top layer is grooved with at least one diametrical groove scored deep enough to penetrate the top layer to aid it's breaking up and disassociation from the bottom layer.

9. The tablet recited in claim 7, wherein the top surface of the tablet is multiply grooved with diametrically arranged depressions scored deep enough to extend through the mid-layer and into the bottom layer.

* * * * *

UNITED STATES PATENT AND TRADEMARK OFFICE
CERTIFICATE OF CORRECTION

PATENT NO. : 4,503,031

DATED : March 5,1985

INVENTOR(S) : Jacob A. Glassman

It is certified that error appears in the above-identified patent and that said Letters Patent is hereby corrected as shown below:

In the drawings Fig. 6, should appear as show on the attached sheet instead of as in the patent.

Signed and Sealed this

Twenty-fourth Day of September 1985

[SEAL]

Attest:

DONALD J. QUIGG

Attesting Officer

Commissioner of Patents and Trademarks—Designate